US00PP12444P2

(12) United States Plant Patent
Utecht

(10) Patent No.: US PP12,444 P2
(45) Date of Patent: Mar. 12, 2002

(54) GERANIUM PLANT NAMED 'FISMERK'

(75) Inventor: Angelika Utecht, Montabaur (DE)

(73) Assignee: Floris AG, Binningen (CH)

( * ) Notice: Subject to any disclaimer, the term of this patent is extended or adjusted under 35 U.S.C. 154(b) by 0 days.

(21) Appl. No.: 09/773,010

(22) Filed: Jan. 31, 2001

(51) Int. Cl.[7] ..... A01H 5/00
(52) U.S. Cl. ..... Plt./330
(58) Field of Search ..... Plt./330, 328

(56) References Cited

U.S. PATENT DOCUMENTS

| | | | | | |
|---|---|---|---|---|---|
| PP5,758 P | * | 7/1986 | Buck | Plt./330 |
| PP5,940 P | * | 4/1987 | Schumann | Plt./330 |
| PP6,397 P | * | 11/1988 | Craig | Plt./330 |
| PP7,609 P | * | 7/1991 | Winner | Plt./330 |
| PP8,192 P | * | 3/1993 | Holden | Plt./330 |
| PP8,727 P | * | 5/1994 | Schumann | Plt./330 |
| PP9,151 P | * | 5/1995 | Enthoven | Plt./330 |
| PP9,489 P | * | 3/1996 | Endisch et al. | Plt./330 |
| PP9,774 P | * | 12/1996 | Utecht | Plt./330 |

OTHER PUBLICATIONS

GTITM UPOVROM Citation for 'Fismerk' as per QZ PBR 991049; Jul. 20, 1999.*
Fischer–Schmülling Plant Alliance Catalog featuring 'FISMERK' on p. 14 (2001).
Official Gazette of the Community Plant Variety Office Oct. 15, 1999; European Union Application, denomination, decision for 'FISMERK'.
German Application for 'FISMERK' Sep. 15, 1998.
German Proprosed Denomination for 'FISMERK' Aug. 15, 1999.
Plant Varieties Journal, Jan. 2001, No. 38, pp. 51–52 (Canada).

* cited by examiner

*Primary Examiner*—Bruce R. Campell
*Assistant Examiner*—Kent L. Bell
(74) *Attorney, Agent, or Firm*—Foley & Lardner

(57) ABSTRACT

A new and distinct cultivar of geranium plant named 'Fismerk', as described and illustrated, and particularly characterized by the combined features of intense orange-red, semi-double flowers, semi-spherical inflorescence, early and rich flowering, and relatively compact growth habit in the beginning, therefore well suited for early cultivation.

1 Drawing Sheet

BACKGROUND OF THE INVENTION

The present invention comprises a new and distinct cultivar of geranium, botanically known as *Pelargonium zonale*, and hereinafter referred to by the cultivar name 'Fismerk'.

'Fismerk' is a product of a planned breeding program which had the objective of creating new geranium varieties with scarlet flower color, compact habit, and in general suitable for early sale. 'Fismerk' originated from a hybridization made by the inventor Angelika Utecht in a controlled breeding program in Galdar, Gran Canaria, Spain, in 1995.

The female parent was a hybrid seedling, no. 990-1 (unpatented), derived from a cross between 'Fisnida' (unpatented) and 'Volcano' (U.S. Plant Pat. No. 5,940). Both varieties have orange-red flowers, the former single-type flowers, the latter semi-double ones. The hybrid seedling was charaterized by red, single-type flowers, large inflorescences, and medium green, zoned foliage. The male parent of 'Fismerk' was the hybrid seedling no. 1383-2 (unpatented), which was characterized by orange-red, semi-double flowers, foliage with distinct zonation, and medium tall plant habit.

'Fismerk' was selected as one flowering plant within the progeny of the stated cross by Angelika Utecht in 1996 in a controlled environment in Galdar, Gran Canaria, Spain.

The first act of asexual reproduction of 'Fismerk' was accomplished when vegetative cuttings were taken from the initial selection in the fall of 1996 in a controlled environment in Galdar, Gran Canaria, Spain, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fismerk' are firmly fixed and are retained through successive generations of asexual reproduction.

'Fismerk' has not been observed under all possible environmental conditions. The phenotype may vary significantly with variations in environment such as temperature, light intensity and day length.

BRIEF DESCRIPTION OF THE INVENTION

The following observations, measurements, and comparisons describe plants grown in Hillscheid, Germany, and in Langley, British Columbia, Canada, under greenhouse conditions which approximate those generally used in commercial practice.

The following traits have been repeatedly observed and are determined to be basic characteristics of 'Fismerk' in combination distinguish this geranium as a new and distinct cultivar:

1. Bright orange-red, semi-double flowers;
2. Large, semi-spherical umbels;
3. Medium-green foliage with distinct zonation;
4. Compact to medium plant habit during cultivation in green-house, grows outdoors with medium vigor;
5. Early and rich flowering as a pot plant; and
6. Suitable for early sale, due to the early flowering and requiring relatively little space during cultivation.

Of the many commercial cultivars known to the present inventor, the most similar in comparison to 'Fismerk' are the varieties 'Mercury', U.S. Plant Pat. No. 5,929, and 'Fisgrand', U.S. Plant Pat. No. 8,760.

In comparison to 'Mercury', 'Fismerk' has a somewhat taller plant habit, rounder umbels, and leaves with distinct zonation, while 'Mercury' has no zonation. In comparison to 'Fisgrand', 'Fismerk' has a more intense flower color, shorter peduncles, smaller leaves, and a more compact plant habit.

In comparison to the male parent, 'Fismerk' has smaller foliage, longer peduncles, and slightly weaker zonation.

BRIEF DESCRIPTION OF THE DRAWING

The accompanying photographic drawing shows typical flower and foliage characteristics of 'Fismerk' with colors being as true as possible with an illustration of this type. The measurements were taken in Langley, British Columbia, Canada, on Jul. 20, 2000, 15 weeks after planting of rooted cuttings into 6 inch pots. The plants had not been pinched.

In the following description color references are made to The Royal Horticultural Society Colour Chart (R.H.S.). The color values were determined indoors from plants developed in a green-house in May 2000 in Hillscheid, Germany.

Classification:

*Botanical.*—A hybrid of the species *Pelargonium zonale* L'Hérit.

*Commercial.*—Zonal geranium, cv. 'Fismerk'.

Inflorescence:

*Umbel.*—Shape: Semi-spherical. Average diameter: 113 mm. Average depth: 65 mm. Peduncle length: 157 mm. Peduncle color: Light to medium green, RHS 143 A. Pedicel length: 31 mm. Pedicel color: Light green, RHS 143 B, with slight infusion of anthocyanin, brownish, RHS 179 B (very weak) near the upper end. Number of flowers per umbel: About 30–40. Lastingness of the umbel: Approximately 18–20 days at 18° C.

*Corolla.*—Average diameter: 44 mm. Form: Semi-double. Shape: Round outline, inner petals somewhat irregularly arranged. Number of petals: 8–11. Size of petals: Upper petals are 22–24 mm long, 20–22 mm wide, lower petals are 23–25 mm long, 22–24 mm wide. Shape of petals: Obovate, attenuate base, rounded upper end, margin entire. Color (general tonality from a distance of three meters): Intense orange-red. Color of upper petals: RHS 43 A. Markings of upper petals: A weak rose-red macule, RHS 57 B, at the base. Color of lower petals: RHS 43 A. Markings of lower petals: No markings or a very weak dot, near RHS 57 B. Color of lower surface of petals: Mainly from RHS 43 A to RHS 43 B. Number of petaloids: 1–3. Color of petaloids: Upper surface RHS 43 A, lower surface RHS 43 B. Number of sepals: 5. Color of sepals: Outer surface green, RHS 137 D, with slight infusion of anthocyanin, RHS 179 B, at the largest sepal, inner surface light green, RHS 153 B, with a slight infusion of anthocyanin, RHS 179 B, at the base. Size of sepals: 10–12 mm long, 4–5 mm wide for the largest, upper sepal, 2–3 mm wide for the other sepals. Shape of sepals: Linear to lanceolate, acute tip, truncate base, surface with weak, short pubescence, margin entire.

*Bud: (just before petals unfold).*—Shape: Elliptical to round. Color (lower part — sepals): Light green, from RHS 143 A to RHS 143 B. Color (upper part — petals): Rose-red, RHS 46 C. Length: 16 mm. Width: 13 mm.

*Reproductive organs.*—Androecium: 3–5 fertile anthers or petaloids, whitish filaments, yellow-orange pollen, RHS 30 A, moderate pollen production. Gynoecium: 5–6-lobed red stigma, reddish style, RHS 44 A, one pistil per flower. Fertility/seed set: Rarely a few seeds are developed, oblong shape, 4–5 mm long, brown, RHS 177B.

*Spring flowering response period.*—In Hillscheid, Germany, in 2000, plants had on average 0.6 flowers opened 8 weeks after planting of rooted cuttings.

*Outdoor flower production.*—Medium flowering throughout the summer, the flower count in 2000 in Hillscheid, Germany, indicated about 4 inflorescences per plant in mid May.

*Durability.*—Good stability of flower color, no fading, may be burnt by the sun, however, no shattering, fair rain resistance.

*Lastingness of the individual bloom.*—Approximately 8 days at 18° C.

*Fragrance.*—None.

Plant:

*Foliage.*—Form: Kidney-shaped, with very weak lobes. Base: Cordate, open gap between the lower lobes. Margin: Bicrenated, distinctly wavy. Texture: Slightly velvety. Size of leaf: 86 mm wide, approximately 55 mm long. Color of upper surface: Medium-green, approximately RHS 137 B. Color of undersurface: RHS 137 D. Color of zonation: Medium distinct, brown, about RHS 166 A. Petiole size: 50–60 mm in length, 3 mm in diameter. Petiole color: RHS 143 C.

*General appearance and form.*—Stem color: Green, RHS 143 A. Internode length: 10–15 mm. Branching pattern: 5.3 branches. Plant size: 21.5 cm in height, as measured from the soil to the surface of the foliage canopy, without the inflorescences; 32.5 cm wide.

Disease/pest resistance/susceptibility: None observed to date.

I claim:

1. A new and distinct cultivar of geranium plant named 'Fismerk', as described and illustrated.

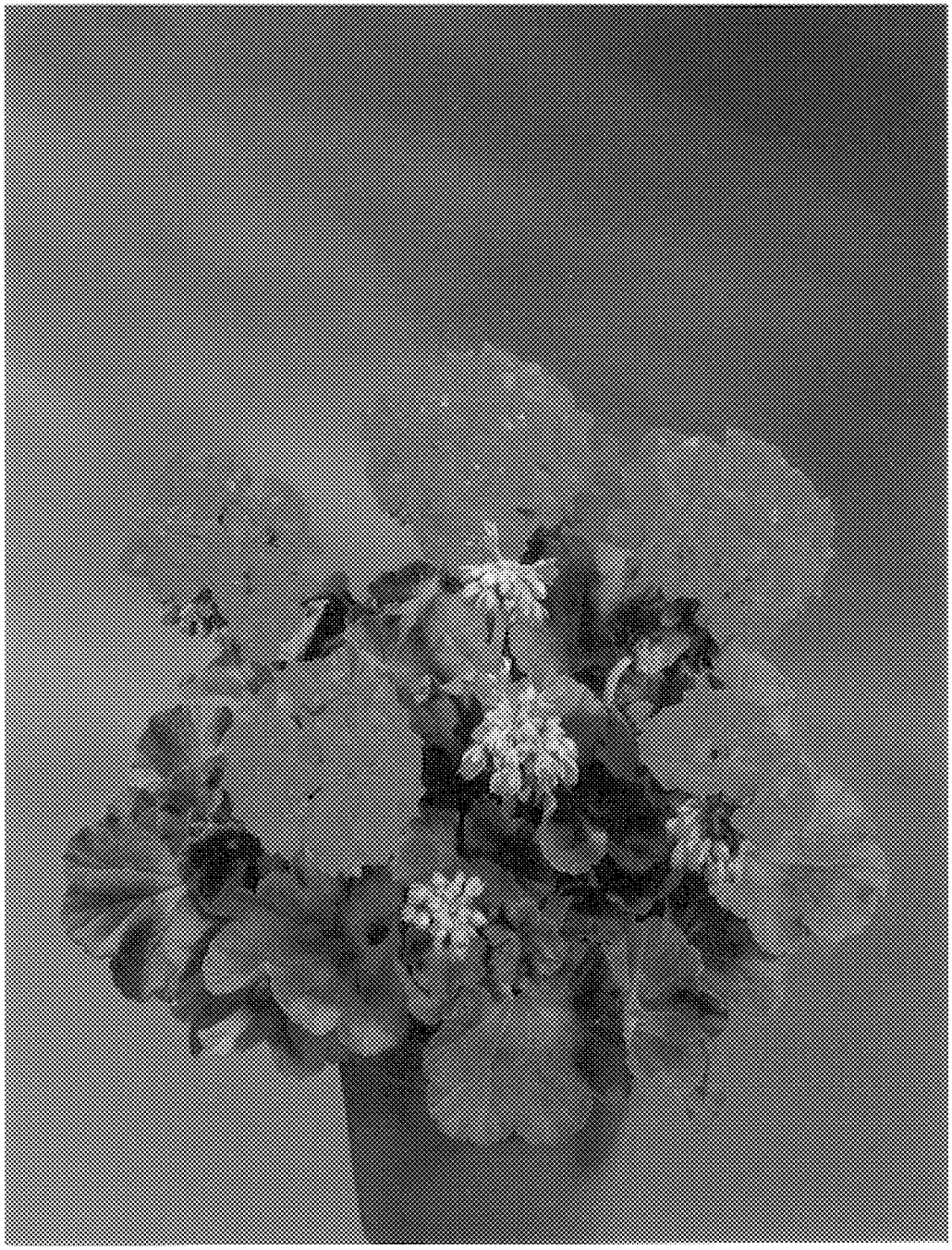

* * * * *